US010278835B2

(12) United States Patent
Lunau et al.

(10) Patent No.: US 10,278,835 B2
(45) Date of Patent: May 7, 2019

(54) MEASUREMENT AND ORDERING SYSTEM FOR ORTHOTIC DEVICES

(71) Applicant: VISION QUEST INDUSTRIES INCORPORATED DBA VQ ORTHOCARE, Irvine, CA (US)

(72) Inventors: Kevin R. Lunau, Valley Center, CA (US); Wallace R. Fischer, Amesville, OH (US); Michael S. Skahan, Ramona, CA (US)

(73) Assignee: VISION QUEST INDUSTRIES INCORPORATED DBA VQ ORTHOCARE, Irvine, CA (US)

( * ) Notice: Subject to any disclaimer, the term of this patent is extended or adjusted under 35 U.S.C. 154(b) by 0 days.

(21) Appl. No.: 15/636,816

(22) Filed: Jun. 29, 2017

(65) Prior Publication Data

US 2018/0000613 A1 Jan. 4, 2018

Related U.S. Application Data

(60) Provisional application No. 62/356,480, filed on Jun. 29, 2016.

(51) Int. Cl.
*A61B 5/107* (2006.01)
*A61F 2/50* (2006.01)
(Continued)

(52) U.S. Cl.
CPC .......... *A61F 2/5044* (2013.01); *A61F 5/0106* (2013.01); *A61F 5/0123* (2013.01); *G06F 19/00* (2013.01); *G06F 19/34* (2013.01)

(58) Field of Classification Search
CPC .............................. G03B 15/14; A61B 5/1079
See application file for complete search history.

(56) References Cited

U.S. PATENT DOCUMENTS

| 8,417,109 | B2 * | 4/2013 | Takatsuka | .............. | G03B 15/00 |
|  |  |  |  |  | 396/263 |
| 2007/0019942 | A1 * | 1/2007 | Kurosawa | .............. | G03B 13/02 |
|  |  |  |  |  | 396/287 |

(Continued)

OTHER PUBLICATIONS

VQ Orthocare, eCast™ Custom Brace Instruction Manual, 2015 (12 Pages).

(Continued)

*Primary Examiner* — Minh Q Phan
(74) *Attorney, Agent, or Firm* — Lawrence N. Ginsberg (57) ABSTRACT

A system and method are provided for electronically capturing a subject's anatomy comprising an electronic device with a camera, display screen, and end-user software program to interface with the user. The software program tracks a target placed in view area, and gives visual feedback to the user based on target tracking. The software program includes criteria represented visually, via audio feedback, or haptic feedback, to the user indicating how to position the camera relative to the anatomy. The end-user software program may have means to automatically capture anatomy on the electronic device based on the criteria being met. The end-user software program may have means to electronically transmit the anatomical information to a remote location where said information can be used to build a custom orthotic device. The system may also have the means to detect and distinguish anatomic contours from other objects in the view area.

19 Claims, 8 Drawing Sheets

(51) Int. Cl.
*A61F 5/01* (2006.01)
*G06F 19/00* (2018.01)

(56) References Cited

U.S. PATENT DOCUMENTS

2015/0223730 A1* 8/2015 Ferrantelli ............ A61B 5/1072
600/476
2015/0271588 A1* 9/2015 Burgett ................ A61B 5/1076
381/380

OTHER PUBLICATIONS

OSSUR.COM, Smart Measure, from https://www.ossur.com/prosthetic-solutions/education-support/prosthetic-product-certifications/pro-flex-product-certification/2-uncategorised/1502-smart-measure-test, downloaded Jan. 4, 2018 (3 Pages).

* cited by examiner

MEASUREMENT AND ORDERING SYSTEM FOR ORTHOTIC DEVICES

CROSS REFERENCE TO RELATED APPLICATIONS

This patent application claims the benefit of U.S. Provisional Application. No. 62/356,480 filed Jun. 29, 2016, entitled MEASUREMENT AND ORDERING SYSTEM FOR ORTHOTIC DEVICES. The entire content of Application. No. 62/356,480 is incorporated by reference herein.

BACKGROUND OF THE INVENTION

1. Field of the Invention

The present invention relates generally to the measurement of a subject's anatomy. An example is when measurements need to be taken of the anatomy to build a custom orthotic device tailored to the specific patient's anatomy. The present invention discloses a novel, convenient, electronic means to measure the anatomy.

2. Description of the Related Art

The most commonly practiced methods of measuring a patient's anatomy include casting, manual measurements, measuring devices, and digitizing the anatomy.

The first method of casting involves pre-marking landmarks on the patient's anatomy, for example the knee-center when casting the leg. Then the anatomy is cast with cast tape, allowing the markings to transfer to the inner surface of the cast tape. The cast tape hardens, and is cut off. The empty cast shell is then shipped to the custom brace manufacturer who then fills the cast with plaster, and cuts the cast away to gain a "positive" representation of the patient's leg with landmarks. As can be imagined, this gives an intimate and detailed model of the patient's anatomy, but is a slow, cumbersome, and expensive process.

Another method involves manually measuring one or more locations on the patient's anatomy, then recording and sending the information to the custom brace manufacturer. This is a much more straightforward process, but with the large disadvantage of omitting much of the patient's anatomical curves and contours. This could lead to an ill-fitting custom brace which has a higher likelihood of being rejected by the patient.

Another method involves the patient being physically present during the building process. This is of course the ideal scenario for the best-fitting brace, but is usually not feasible due to geographical and schedule limitations.

Still another method involves using a 3-dimensional scanning system to capture the entire leg anatomy. The major disadvantage of a full 3D digitizing setup is the cost and complication of the system.

There has been a partial response to these problems. U.S. Pat. Publication. No. US 2014/0063220 A1, issued to Taylor, entitled, "Method and Device for Ordering a Custom Orthopedic Device," discloses a method and device for digital measuring and ordering a custom orthopedic device.

An alternate embodiment is described in Taylor that deals with the generation of a three-dimensional model. Markers are added to the anatomy, but only to act as "dumb" reference points for generating the three-dimensional model from multiple views of the anatomy. Taylor does not teach about a smart target that is interpreted and tracked by the software on the fly, to determine distance and position of the camera relative to the anatomy, and to give real-time feedback to the user about how to correct the camera position in order to capture a well-oriented photo of the anatomy. Rather, the markers are used passively to construct a 3D model.

Another embodiment in Taylor includes depth of field measurements from the camera to determine position of anatomy. This is a different method of using the focus and zoom of the camera to determine the size of the anatomy in the display view area. The embodiment does not disclose anything regarding target patterns used in a real-time augmented reality scenario as the present invention uses.

SUMMARY OF THE INVENTION

In a broad aspect, the present invention describes a system to electronically capture and measure a subject's anatomy using sensors and feedback loop(s) from an electronic device to the user. The feedback loops can be visual, auditory, sensory/haptic, or a combination.

In another broad aspect the present invention is embodied as a system for electronically capturing a subject's anatomy. The system includes: a) an electronic device including: i) a camera configured to capture a subject's anatomical information; ii) a display screen; iii) an input method and, iv) an end-user software program configured to interface with a user via the display screen and input method, and to process information captured on the camera; and, b) at least one target pattern.

The end-user program includes: i) a user interface to provide user control of program functions; and ii) software programming to: 1) recognize and track the target pattern in a view area of the camera; and, 2) provide feedback to the user on at least one of the following, based on the tracking of the target pattern: size, shape, or position of the target pattern, for the purpose of directing the user to move the camera appropriately relative to the target pattern, thereby resulting in an optimized view of the anatomical information; iii) means to capture the optimized anatomical information via the camera; and, iv) means to extrapolate the target pattern size, shape, or position into measurements of the anatomy size, shape, or position.

In another broad aspect, the present invention is embodied as a method for electronically capturing a subject's anatomical information, comprising the steps of: a) providing an electronic device comprising a camera, display screen, a method for data input, an end-user software program, the program including position feedback criteria displayed on the screen; b) placing a subject's anatomy and a target pattern within a view area of the camera; c) adjusting the position of the camera until the position feedback criteria are met, relative to the target pattern, and the program indicates to the user that the camera is in a position to provide an optimized view of the anatomical information; and, d) capturing the optimized view of the anatomical information.

In a preferred embodiment, the system comprises a unique series of features to allow accurate and convenient measurement of the anatomy via a camera, an electronic device with an associated end-user software program installed, and a specific target area that the pattern recognition software embedded in the end-user software program recognizes.

The target pattern(s) is/are a known size and shape programmed into the end-user software program.

The pattern recognition function of the end-user software scans the image in real time for the target pattern and places markers on the display based on the embedded target parameters. These markers guide the user to orient the camera such that relationship to the anatomy is correct for measurement. When the software program determines the camera is correctly placed, it can automatically capture an image or video of the anatomy.

In another broad aspect, the edge detection software function can scan for and detect anatomic edges (i.e. anatomic contours) and determine if the anatomy is fully displayed, or whether it may be blocked or incomplete.

For example, the subject's clothing may be obstructing a portion of the anatomy. If this is the case, the edge detection function of the end-user software program will alert the system user to address the issue before capturing the anatomical data.

The end-user software program also includes a software positioning function that can check for proper position and shape of the anatomy (as opposed to orientation of the camera). For example, the software positioning function can check for proper flexion in the lateral (side) view of the leg. If the leg is in too much flexion, the end-user software program can alert the user.

Other objects, advantages, and novel features will become apparent from the following detailed description of the invention when considered in conjunction with the accompanying drawings.

DETAILED DESCRIPTION OF THE INVENTION

Figure 1:
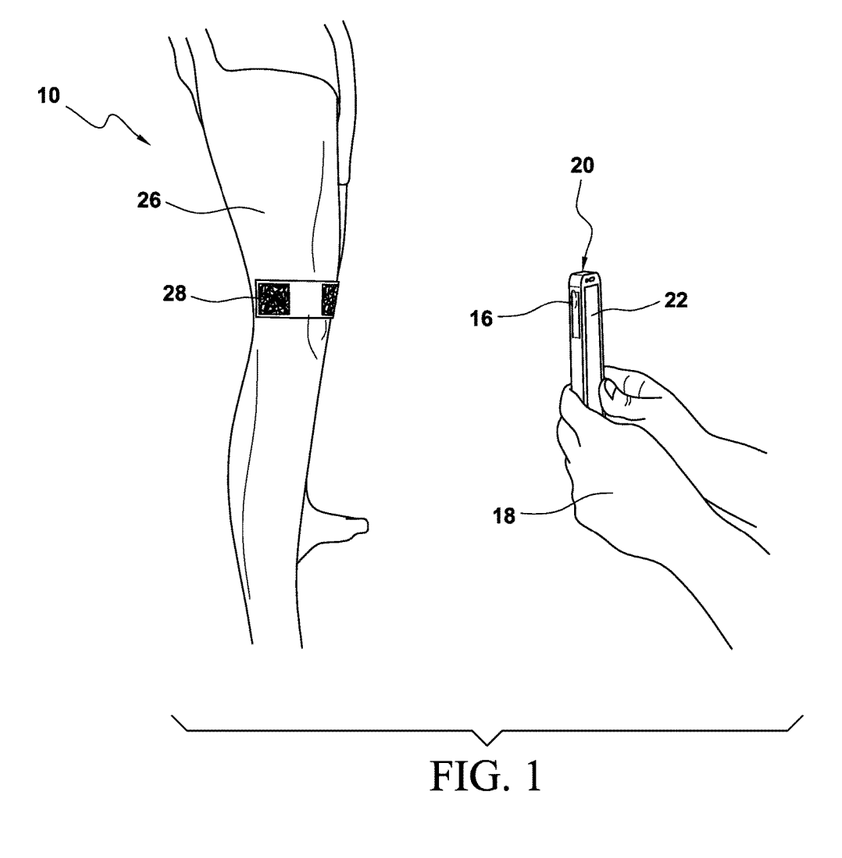
FIG. 1 is a general view of the system of the present invention, and anatomy of the user.

Referring now to the drawings and the characters of reference marked thereon, FIG. 1 illustrates the system of the present invention, designated generally as 10. The user 18 places tape 28 on the anatomy 26. The user 18 then positions electronic device 20 which includes camera 16, to capture the anatomical information 26.

Figure 2:
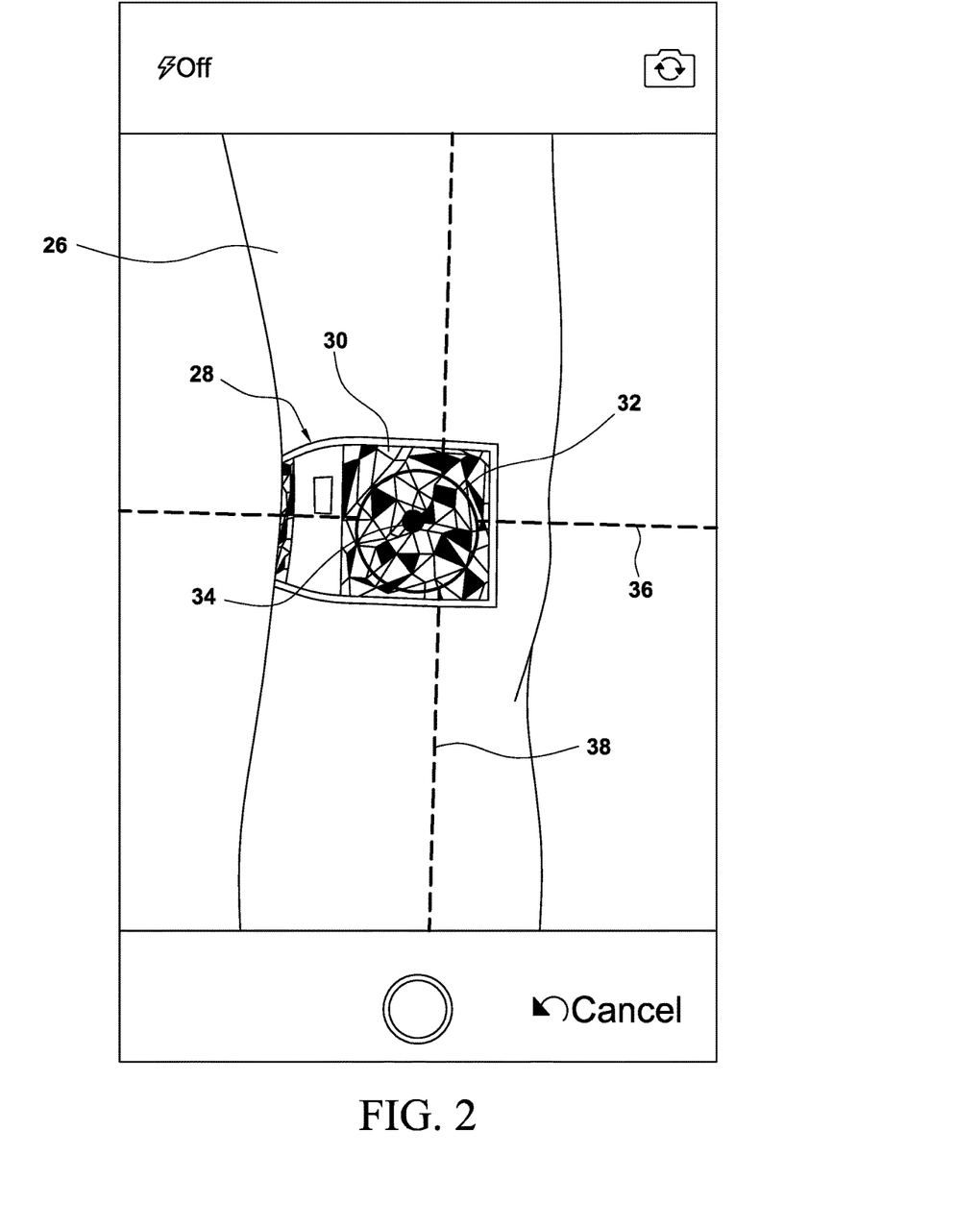
FIG. 2 shows the display screen with an anterior (front) view of the anatomy, the target pattern, and feedback markers.

Referring now to FIG. 2, tape 28 is applied to the anatomy. An end-user software program installed on electronic device 20 is used to recognize the size, shape, or position of at least one target pattern 30 on tape 28. The electronic device program finds the target pattern 30 and uses it to provide feedback to the user for the purpose of directing the user 18 to move the camera 16 to result in an optimized view of the anatomical information 26. One way to give feedback is to place feedback markers on display 22 for the user 18 to orient the camera 16. These feedback markers guide the user 18 to re-orient the camera 16 until it is in a suitable or optimized position to capture the anatomy 26.

Examples of feedback markers for an anterior (front) view include several display items which can act independently, or in conjunction with one another. One type of feedback marker could be a pitch line 36, which guides the user to position the camera at the correct pitch angle (i.e. pivoting about an axis parallel to the intersection of coronal and transverse planes). Still another feedback marker could be a yaw line 38, which guides the user to position the camera at the correct yaw angle (i.e. pivoting about an axis parallel to the intersection of coronal and sagittal planes).

The pitch line 36 and yaw line 38 together guide the user to position the camera at the correct roll angle (i.e. pivoting about an axis parallel to the intersection of the transverse and sagittal planes).

Figure 3:
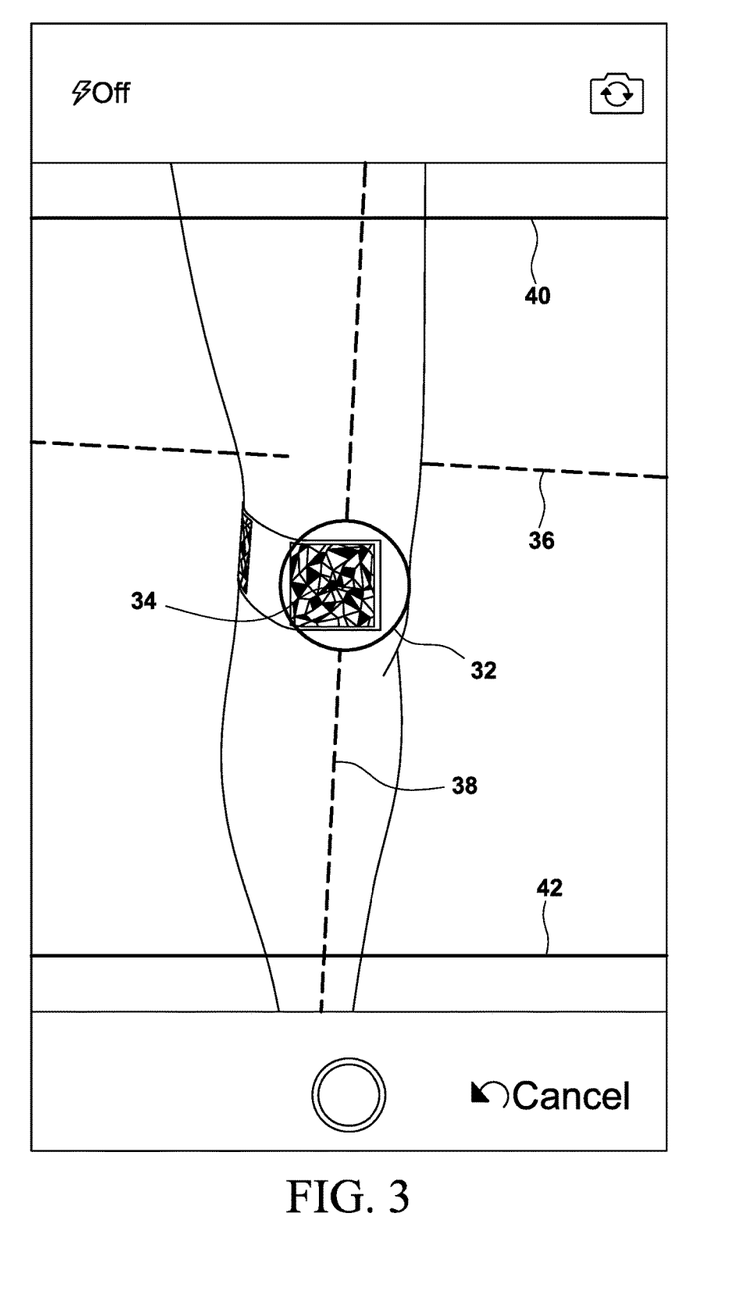
FIG. 3 shows the display screen with an anterior (front) view of the anatomy, showing a feedback marker that needs correction.

Referring now to FIG. 3, another type of feedback marker could be a center zone 32, which is used to guide the user to move the camera to the correct position in the coronal plane (up, down, left, right in the coronal plane). Still another feedback marker could be top distance line 40 and bottom distance line 42. These lines give the user feedback as to how far back the camera needs to be placed (movement perpendicular to the coronal plane) in order to capture enough of the anatomy for proper measurement.

A visual technique to communicate this to the user is by the use of position and color on the display 22. One or all of the above markers can change attributes, (such as size, position, or color) on display 22 to give the user feedback on how to correct the camera position or angle and capture the anatomy 26 properly.

For example, the feedback markers can turn red if they need correction, and they can move along the display 22 in real-time to alert the user which way to re-orient the camera to correct the position. FIG. 2 shows a mostly correctly-positioned camera: pitch line 36, yaw line 38, center marker 34 are all green and in the correct position. However, top distance line 40 and bottom distance line 42 are not shown on the screen, indicating the camera is too close to the anatomy.

Now referring to FIG. 3, the top distance line 40 and bottom distance line 42 are shown, and colored green, for example. These top/bottom distance lines 40, 42 are controlled by the end-user software program based on the known size, shape, or position of the target pattern 30. The program scans target pattern 30 as the camera 16 is moved perpendicular to the coronal plane, and re-positions/re-colors, or changes attributes of these lines 40, 42 accordingly, based on the relative size, shape, or position of the target pattern 30. As the camera 16 is moved away from the anatomy 26, the target pattern 30 becomes smaller and lines 40, 42 are moved closer together. As the camera is moved closer to the anatomy, the lines 40, 42 are moved further apart. If the target pattern 30 is within a predetermined size range (based on distance of camera from anatomy), the lines 40, 42 are colored green. If the camera is too far away from the anatomy, the lines 40, 42 are colored red. If the camera is too close, the lines 40, 42 are not displayed. In either case, the end-user software program will not allow the anatomy to be captured.

In FIG. 3 for example, all other feedback markers are colored green, except the red pitch line 36. The pitch line 36 is red and is shown above the knee center marker 34, which means the camera is tilted (pitched) too low. A software function embedded in the end-user software program can use data from a sensor in the electronic device to determine whether the camera is tilted too high or too low. If the camera is tilted beyond pre-set angle limits, the pitch line 36 is colored red for example, and re-positioned on the display 22 according to the degree of improper tilt, to alert the user to correct the pitch angle. If the camera is tilted too far down, the pitch line 36 will be turned red and moved up on the display 22, out of range. If the camera is tilted too far up, the pitch line 36 will be turned red and moved down, out of range.

Similarly, the yaw line 38 is linked to the relative shape of the target pattern 30. If the displayed target shape deviates too much from the pattern recognition software's predefined shape, the yaw line 38 will move accordingly and become red, preventing the anatomical data from being captured.

Figure 4:
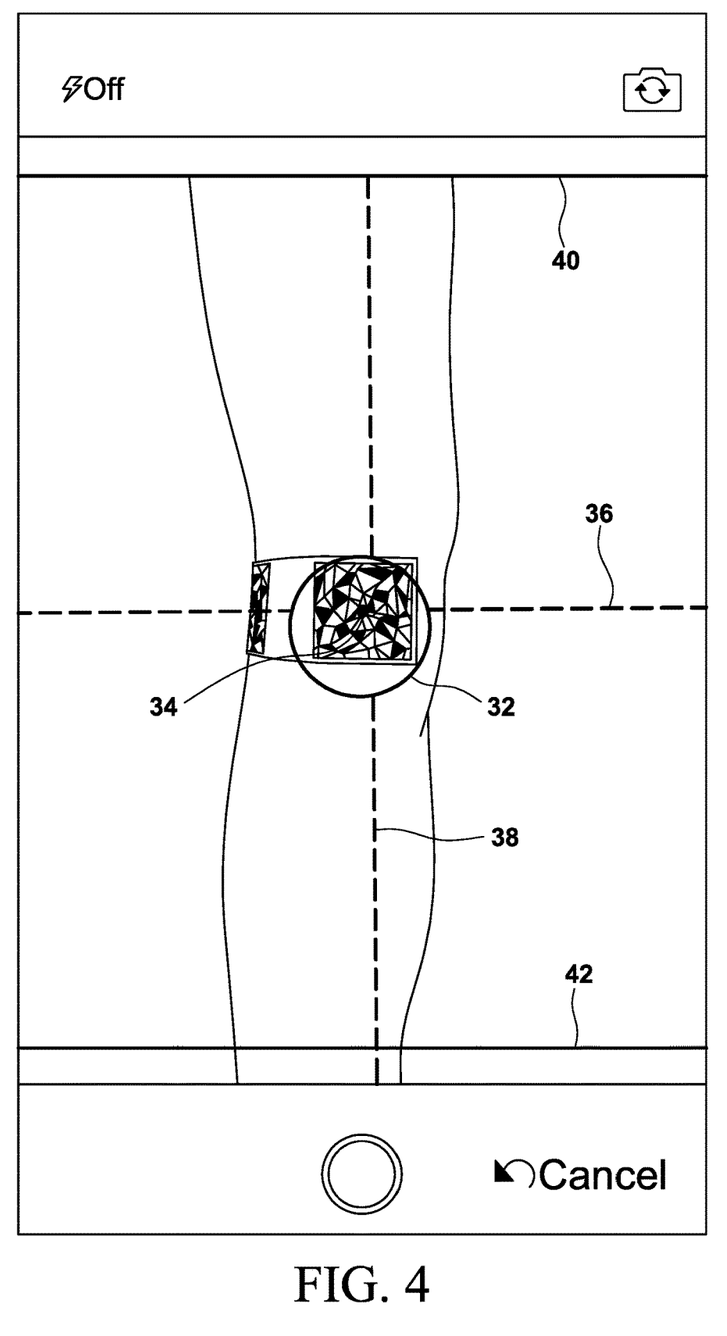
FIG. 4 shows the feedback markers with the orientation corrected.

Now referring to FIG. 4, all feedback markers are green, so the camera is in the correct position for capturing the data that described the anatomy 26. The feedback markers are visual displays, or auditory or haptic feedback cues to the user, and are driven by predefined criteria in the end-user software program of what constitutes a well-defined or optimized anatomical view. Once the predefined criteria is met, the program can allow the camera to automatically capture the anatomy 26 by taking a photograph or video of the anatomy 26, along with some or all of the feedback markers or other data or metadata such as electronic measurement information. For example, the stored image could include just the center marker 34 and the top/bottom distance lines 40, 42.

Figure 5:
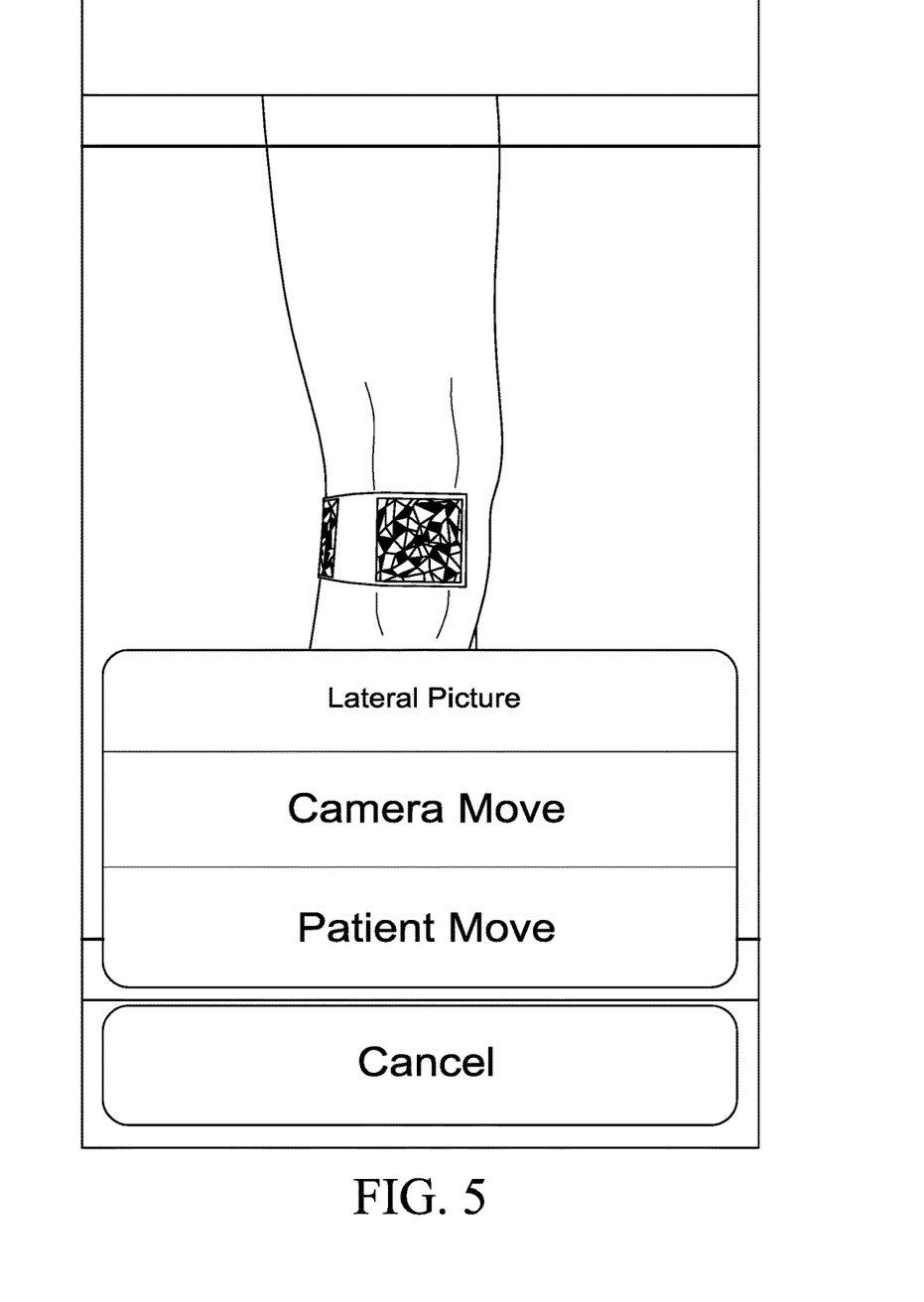
FIG. 5 shows a query screen asking the user to choose how to orient the next photo.

Referring now to FIG. 5, the successful anterior view is complete, and now the end-user software program queries the user to either move the camera or the patient to take a lateral (side) view.

Figure 6:
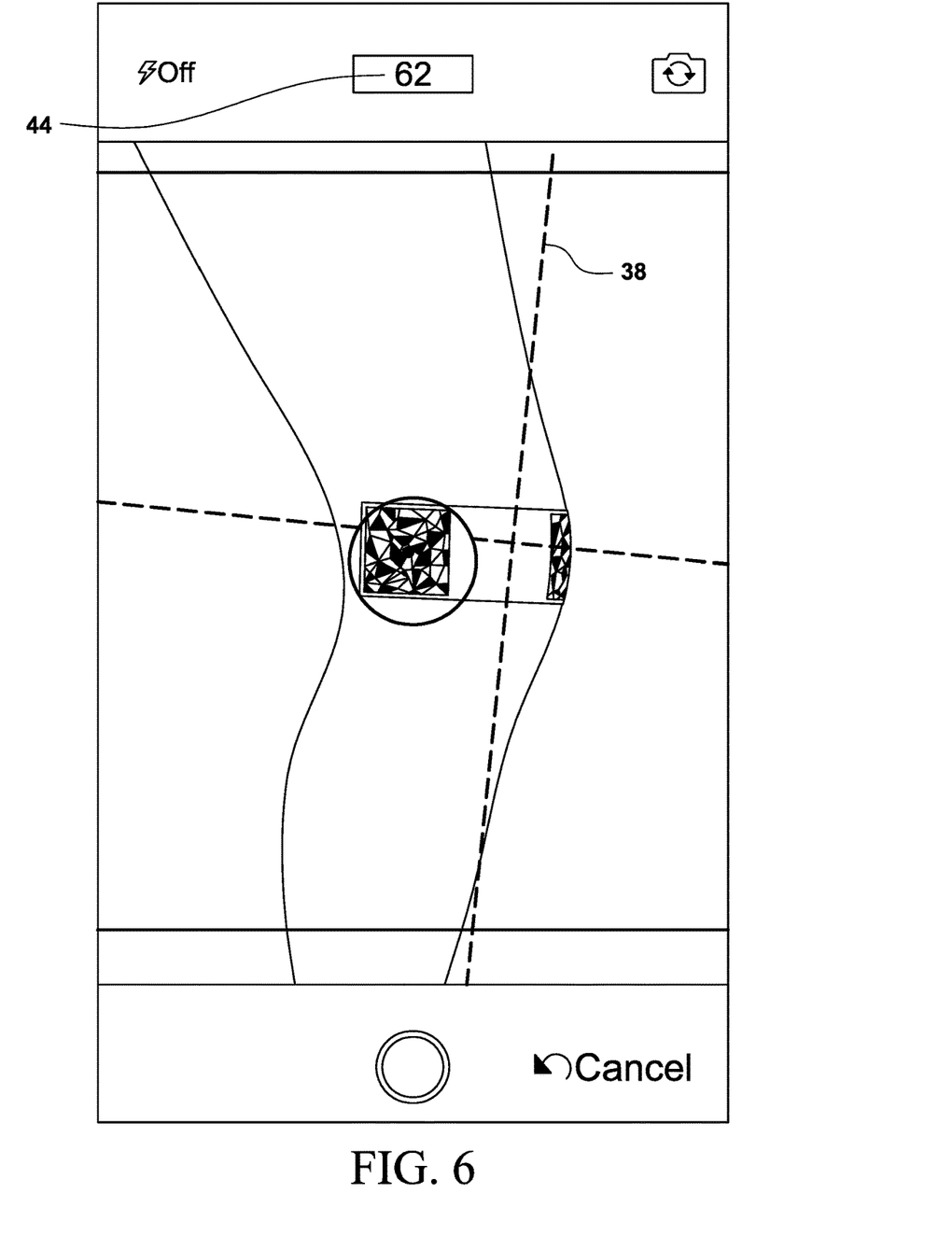
FIG. 6 shows the display screen with an lateral (side) view of the anatomy, showing a feedback marker that needs correction.

Referring to FIG. 6, if the camera is moved, the end-user software program stores the anterior view camera orientation via the on-board compass or other sensor, and displays another feedback marker of the lateral yaw angle 44. This guides the user to pivot the camera around to the lateral side of the anatomy, somewhere close to 90-degrees from where the anterior anatomy 26 was captured. FIG. 6 shows the lateral yaw angle 44 as 62-degrees, which is not within the tolerance to capture the lateral anatomy. Accordingly, the yaw line 38 is off-center and displayed in red, preventing the anatomy from being captured.

Figure 7:
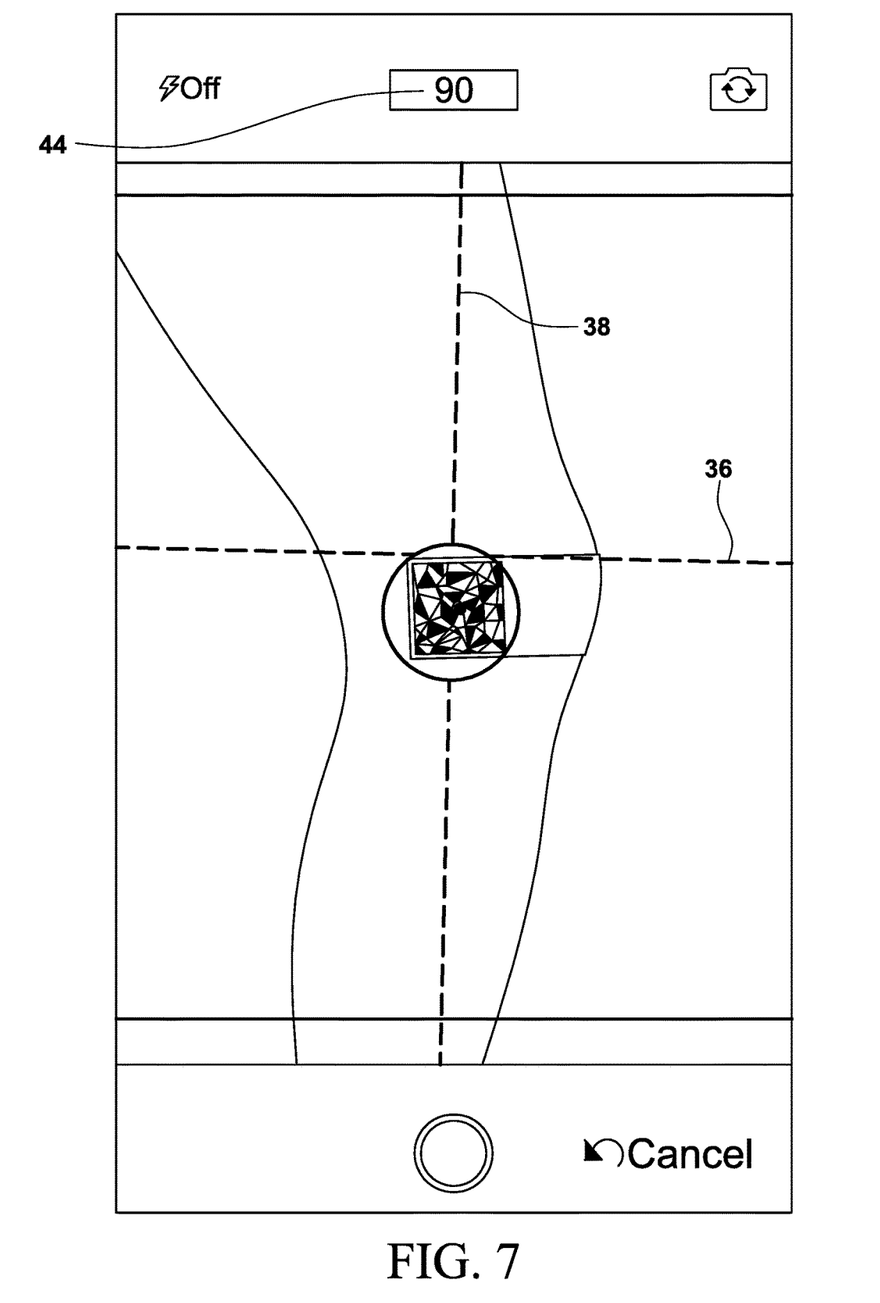
FIG. 7 shows the feedback markers with the orientation corrected.

FIG. 7, however, shows a lateral yaw angle of 90-degrees, which would allow the lateral anatomy to be captured. Of course, all other feedback markers described above (such as pitch line 36) are still active, assuring the camera will be correctly-oriented to the lateral anatomy.

Referring back to FIG. 5, the other option to capture lateral anatomy would be to choose "Patient Move". If this option is chosen, the end-user software program does not use the lateral yaw angle 44 since the patient is moving, not the camera.

The pattern recognition function of the end-user software program, combined with pre-defined criteria relative to known target pattern 30, correctly-oriented anatomy 26, and electronic measurement information such as feedback marker displays can all be stored with the captured photographs or videos. For example, relative to the target pattern in the anterior view of the anatomy, the pre-defined criteria as programmed in the software function, as measured by the sensors in the electronic device 20, and as shown on the display 22, are used to control and give feedback to the user 18 on the six basic degrees of freedom: yaw, pitch, roll angles, and linear movement normal to coronal, sagittal, and transverse planes. This can be translated to the camera's: pitch, yaw, roll, distance, height, or horizontal position, all relative to the target pattern.

The pattern recognition function of the end-user software program includes known size, shape, or position parameters of the target pattern 30. These known parameters of the target pattern are used as a baseline to extrapolate the size, shape, or position of the anatomical information into full-scale (i.e. actual size) measurements. This captured anatomical data and electronic measurement information can then be used to measure the anatomy 26 for various purposes. One such purpose is to build a custom orthotic device such as a custom knee brace.

The programming to use the known size, shape, or position parameters of the target pattern 30 to extrapolate the size, shape, or position of the anatomical information can exist on the electronic device 20, and/or on a remote device or system for further processing.

Note that the parameters can also be used to change the scale of the anatomy if desired. For example, this can be useful for post-operative patients that are anticipated to have muscle atrophy, or other recovering patients that are anticipated to have muscle hypertrophy. Different scaling can also be used to accommodate patients that are anticipated to gain or lose weight.

Scaling can be done isotropically (all axes equal), or anisotropically (axes have different scaling factors). Anisotropic scaling could be used to more closely mimic the anatomy changes for a particular purpose. For example, during weight loss, a thigh shrinks in girth, but not in length, so non-uniform scaling would give a better representation and corresponding fit.

Each of the electronic components (display 22, sensors, camera 16, etc.) can be remotely located, i.e. they need not be located on the same device.

Figure 8:
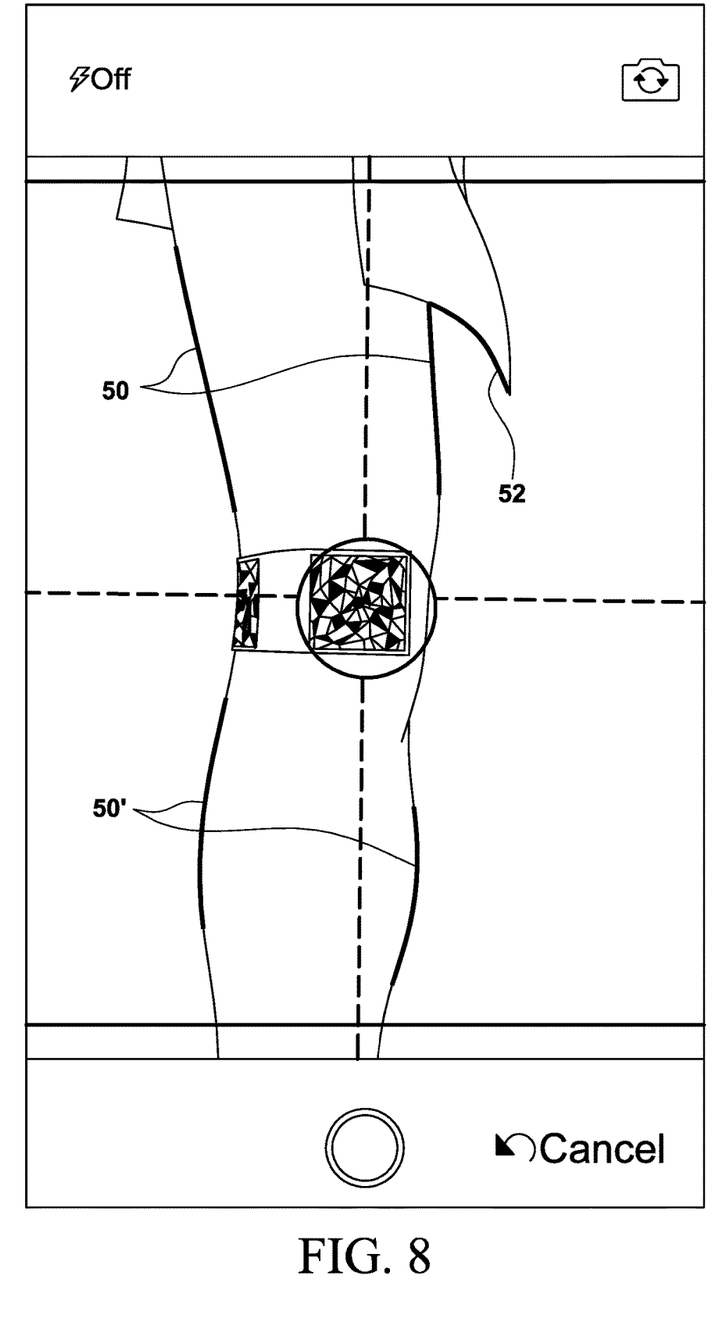
FIG. 8 is the display screen with an anterior (front) view of the anatomy, showing anatomic and non-anatomic contours.

In another embodiment, shown in FIG. 8, the edge recognition function of the end-user software program can be programmed to detect, distinguish, and analyze anatomic edges (i.e. anatomic contours) versus items in the background of the view. This edge detection functionality can be used to determine if the anatomy is correctly displayed prior to capture. For example, the function can scan for contrast, color, brightness, or other parameters denoting the edge of the anatomy. The software function can then trace the anatomy and the end-user software program may display an outline shape of the anatomy as anatomic edges or anatomic contours 50 and 50'.

If the edge detection function finds a discontinuity in the anatomic contours 50 and 50', it may display this as a non-anatomic contour 52. This may be displayed as a flashing line, or different colored line, or other change to alert the user. The non-anatomic contour 52 may be due to clothing or other item obscuring the anatomy, or may be due to the anatomy being in a non-ideal position, for example if the lateral view shows the leg in too much flexion, this would be undesirable for building a well-fitting custom brace.

There can be a provision to over-ride some or all of the above feedback markers and capture the anatomy anyway. There may also be a flag placed on the captured data/electronic measurement information to alert downstream users that an over-ride was used, and to be vigilant for less-than-ideal data.

Once the anatomy has been captured, the end-user software program may have the means to transmit said captured information and other data to a remote server where it can be processed and used to build a custom orthotic device to fit said anatomy.

This system has the advantage that no physical measurements are taken by the user; all measurements are electronic, based on the size, shape or position of the target and associated programming, so they are easily performed, and quickly changed/repeated if necessary.

This invention has been discussed in relation to building custom orthotic devices, it may have other applications, such as building custom prosthetic devices, or custom-fitted apparel. Furthermore, even though it has been shown in this patent application relative to its application to a knee, it may be used in many orthotic applications, for example, but not limited to other parts of the anatomy such as feet, lower and upper leg, finger, wrist, hand, arm, shoulder, head, etc.

This invention has been discussed in relation to feedback that moves or changes color based on relative position of the camera and target pattern. Other means to provide feedback to the user are also feasible, such as via shapes or animation on display screen, audio signals, or haptic (sense of touch) feedback, or any combinations of the above.

This invention has been discussed using independent sets of measurements. Multiple measurements could be taken such as at the start and end of an activity that would allow comparison and contrast of positions. Study of movement or limitations of movement can be analyzed.

In an embodiment the electronic device is connectable to the internet, and the end-user software program is configured to transfer the optimized view of the anatomical information and electronic measurement information to a remote location.

Other embodiments and configurations may be devised without departing from the spirit of the invention and the scope of the appended claims.

The invention claimed is:

1. A system for electronically capturing a subject's anatomy, comprising:
 a) an electronic device comprising:
  i) a camera configured to capture anatomical information of the anatomy of a subject;
  ii) a display screen; and,
  iii) an end-user software program configured to interface with a user via said display screen and to process information captured on said camera; and,
 b) at least one target pattern for physical placement on a subject's anatomy; wherein said program comprises:
  i) a user interface to provide user control of software functions;
  ii) software programming to:
   recognize and track said at least one target pattern in a view area of said camera; and,
   provide feedback to said user on at least one of the following, based on the tracking of the pattern: size, shape, or position of said at least one target pattern, for the purpose of directing said user to move said camera appropriately relative to said at least one target pattern physically placed on the subject, thereby resulting in an optimized view of said anatomical information;
  iii) means to capture the optimized view of the anatomical information via said camera; and,
  iv) programming to extrapolate a known size, shape, or position of said at least one target pattern physically placed on the subject into electronic measurements of the size, shape, or position of said anatomical information; and, wherein said anatomical information is captured automatically by said end-user software program when a target pattern physically placed on the subject is presented and a predefined set of criteria is met, said predefined set of criteria including one or more of the following, relative to said at least one target pattern physically placed on the subject: camera pitch or camera yaw.

2. The system of claim 1, wherein only electronic measurements of anatomy are taken, and no physical measurements are taken.

3. The system of claim 1, wherein said feedback is expressed to the user on the display screen as color changes.

4. The system of claim 1, wherein said feedback is expressed to the user as haptic feedback.

5. The system of claim 1, wherein said feedback is expressed to the user as visual attribute changes to items on the display screen.

6. The system of claim 1, wherein said feedback is expressed to the user as movement of items on the display screen.

7. The system of claim 1, wherein said feedback is expressed to the user as audio feedback.

8. The system of claim 1, wherein said end-user software program programming is configured to distinguish edges of said anatomy versus the background or other objects within a view area of said camera.

9. The system of claim 1, wherein said anatomical information is captured automatically by said end-user software program when a predefined set of criteria is met, said predefined set of criteria including one or more of the following, relative to said at least one target pattern physically placed on the subject: camera roll, camera distance, camera height, or camera horizontal position.

10. The system of claim 1, wherein said electronic device is connectable to the internet, and said end-user software program is configured to transfer said optimized view of said anatomical information and electronic measurement information to a remote location.

11. The system of claim 1, wherein said anatomical information and electronic measurement information is used to build a custom orthotic device, custom prosthetic device or custom-fitted apparel to fit said subject's anatomy.

12. The system of claim 1, wherein said anatomical information and electronic measurement information is used to capture and compare two or more sets of data points allowing change in movement to be determined.

13. The system of claim 1, wherein the electronic measurements can be scaled.

14. A method for electronically capturing anatomical information of a subject, comprising the steps of:
 a) providing an electronic device comprising a camera, a display screen, and an end-user software program, said software program including position feedback criteria displayed on said display screen;
 b) placing a subject's anatomy and a target pattern within a view area of said camera, said target pattern being physically placed on the subject's anatomy;
 c) adjusting the position of said camera until said position feedback criteria are met, relative to said target pattern physically placed on the subject, and said end-user software program indicates to the user that said camera is in a position to provide an optimized view of anatomical information of a subject; and,
 d) capturing anatomical information
 wherein said anatomical information is captured automatically by said end-user software program when a target pattern physically placed on the subject is presented and a predefined set of criteria is met, said predefined set of criteria including one or more of the following, relative to said at least one target pattern physically placed on the subject: camera pitch or camera yaw.

15. The method of claim 14, wherein said optimized view of anatomical information is used to build a custom orthotic, custom prosthetic device or custom-fitted apparel to fit said anatomy.

16. The method of claim 14, wherein said anatomical information and electronic measurement information is used to capture and compare two or more sets of data points allowing change in movement to be determined.

17. A system for electronically capturing a subject's anatomy, comprising:
an electronic device comprising:
    i) a camera configured to capture anatomical information of the anatomy of a subject via physical placement of a target pattern on the subject's anatomy;
    ii) a display screen; and,
    iii) an end-user software program configured to interface with a user via said display screen and to process information captured on said camera;
wherein said end-user software program comprises:
    i) a user interface to allow user control of software functions;
    ii) software programming to distinguish anatomic contours of said anatomy versus non-anatomic contours within a view area of said camera; and,
    iii) means to capture said anatomical information; and,
wherein said anatomical information is captured automatically by said end-user software program when a target pattern physically placed on the subject is presented and a predefined set of criteria is met, said predefined set of criteria including one or more of the following, relative to said at least one target pattern physically placed on the subject: camera pitch or camera yaw.

18. The system of claim 17, wherein, said anatomical information is used to build a custom orthotic device, custom prosthetic device, or custom-fitted apparel to fit said anatomy.

19. The system of claim 17, wherein said anatomical information and electronic measurement information is used to capture and compare two or more sets of data points allowing change in movement to be determined.

* * * * *